(12) United States Patent
Euteneuer et al.

(10) Patent No.: US 10,413,397 B2
(45) Date of Patent: Sep. 17, 2019

(54) IMPLANTABLE TENDON PROTECTION SYSTEMS AND RELATED KITS AND METHODS

(71) Applicant: Rotation Medical, Inc., Plymouth, MN (US)

(72) Inventors: Charles L. Euteneuer, St. Michael, MN (US); Thomas R. Hektner, Medina, MN (US); Thomas A. Westling, Orono, MN (US); Rebecca McCarville, Spring Park, MN (US); Duane Frion, Brooklyn Center, MN (US)

(73) Assignee: Rotation Medical, Inc., Plymouth, MN (US)

( * ) Notice: Subject to any disclaimer, the term of this patent is extended or adjusted under 35 U.S.C. 154(b) by 212 days.

(21) Appl. No.: 14/798,921

(22) Filed: Jul. 14, 2015

(65) Prior Publication Data

US 2015/0313705 A1    Nov. 5, 2015

Related U.S. Application Data

(63) Continuation of application No. 13/763,414, filed on Feb. 8, 2013, now Pat. No. 9,101,460, which is a
(Continued)

(51) Int. Cl.
*A61F 2/08*     (2006.01)
*A61F 2/00*     (2006.01)

(52) U.S. Cl.
CPC .......... *A61F 2/0805* (2013.01); *A61F 2/0063* (2013.01); *A61F 2/0077* (2013.01);
(Continued)

(58) Field of Classification Search
CPC .......... A61F 2/08; A61F 2/0805; A61F 2/0077
See application file for complete search history.

(56) References Cited

U.S. PATENT DOCUMENTS

| 511,238 A | 12/1893 | Hieatzman et al. |
| 765,793 A | 7/1904 | Ruckel |
| (Continued) | | |

FOREIGN PATENT DOCUMENTS

| CA | 2390508 A1 | 5/2001 |
| EP | 0142225 A1 | 5/1985 |
| (Continued) | | |

OTHER PUBLICATIONS

Alexander et al., "Ligament and tendon repair with an absorbable polymer-coated carbon fiber stent", Bulletin of the Hospital for Joint Diseases Orthopaedic Institute, 46(2):155-173, 1986.
(Continued)

*Primary Examiner* — Bruce E Snow
(74) *Attorney, Agent, or Firm* — Seager, Tufte & Wickhem LLP

(57) ABSTRACT

An implantable tendon protection system includes a body adapted to be implanted within a bursa overlying a tendon of a patient to protect the tendon. The body may be fixed to the tendon with adhesive, sutures, staples, and/or anchors. A surgical kit is provided with such a tendon protection system and an insertion cannula. Methods of protecting a tendon of a patient are also disclosed.

20 Claims, 14 Drawing Sheets

Related U.S. Application Data continuation of application No. 12/684,774, filed on Jan. 8, 2010, now abandoned.

(60) Provisional application No. 61/253,800, filed on Oct. 21, 2009, provisional application No. 61/184,198, filed on Jun. 4, 2009, provisional application No. 61/162,234, filed on Mar. 20, 2009, provisional application No. 61/153,592, filed on Feb. 18, 2009, provisional application No. 61/143,267, filed on Jan. 8, 2009.

(52) U.S. Cl.
CPC ........ *A61F 2/08* (2013.01); *A61F 2002/0072* (2013.01); *A61F 2002/0086* (2013.01)

(56) References Cited

U.S. PATENT DOCUMENTS

| | | |
|---|---|---|
| 1,728,316 A | 9/1929 | von Wachenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 11/1993 | Handlos |
| 5,261,914 A | 12/1993 | Warren |
| 5,269,753 A | 12/1993 | Wilk |
| 5,269,783 A | 12/1993 | Sander |
| 5,279,570 A | 1/1994 | Dombrowski et al. |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | Dematteis |

(56) References Cited

U.S. PATENT DOCUMENTS

| | | |
|---|---|---|
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Grambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 8/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |

(56) References Cited

U.S. PATENT DOCUMENTS

| | | |
|---|---|---|
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,846,171 B2 | 12/2010 | Kullas et al. |
| 7,918,879 B2 | 4/2011 | Yeung et al. |
| 8,080,260 B2 * | 12/2011 | Derwin ............ A61F 2/08 424/423 |
| 8,114,101 B2 | 2/2012 | Criscuolo et al. |
| 8,197,837 B2 | 6/2012 | Jamiolkowski et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2004/0267277 A1 * | 12/2004 | Zannis ............ A61F 2/4618 606/99 |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0113938 A1 * | 5/2005 | Jamiolkowski ......... A61F 2/02 623/23.74 |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | Dedeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mona Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 * | 6/2009 | Trenhaile ............ A61F 2/0063 604/99.01 |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olsen |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer et al. |
| 2012/0248171 A1 | 10/2012 | Bailly et al. |
| 2012/0316608 A1 | 12/2012 | Foley |
| 2013/0153628 A1 | 6/2013 | Euteneuer et al. |
| 2013/0158554 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |

(56) References Cited

U.S. PATENT DOCUMENTS

| | | |
|---|---|---|
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005506122 A | 3/2005 |
| JP | 2006515774 A | 6/2006 |
| WO | 8505025 A | 11/1985 |
| WO | 0176456 A2 | 10/2001 |
| WO | 0234140 A2 | 5/2002 |
| WO | 03105670 A2 | 12/2003 |
| WO | 04000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |

OTHER PUBLICATIONS

Bahler et al., "Tabecular bypass stents decrease intraocular pressure in cultured himan anterior segments", Am. J. Opthalmology, 138(6):988-994, Dec. 2004.

Charmay et al., "Digital contracture deformity after implantation of a silicone prosthesis: Light and electron microscopic study", The Journal of Hand Surgery, 3(3):266-270, May 1978.

D'Ermo et al., "Our results with the operation of ab externo," Ophthalmologica, 168:347-355, (year of pub. sufficiently earlier than effective US filing date and any foreign priority date) 1971.

France et al., "Biomechanical evaluation of rotator cuff fixation methods", The American Journal of Sports Medicine, 17(2):176-181, Mar.-Apr. 1989.

Goodship et al., "An assessment of filamentous carbon fibre for the treatment of tendon injury in the horse", Veterinary Record, 106:217-221, Mar. 8, 1980.

Johnstone et al., "Microsurgery of Schelmm's canal and the human aqueous outflow system", Am. J. Opthalmology, 76(6):906-917, Dec. 1973.

Kowalsky et al., "Evaluation of suture abrasion against rotator cuff tendon and proximal humerus bone", Arthroscopy: The Journal of Arthroscopic and Related Surgery, 24(3):329-334, Mar. 2008.

Lee et al., "Aqueous-venous and intraocular pressure. Preliminary report of animal studies", Investigative Ophthalmology, 5(1):59-64, Feb. 1966.

Maepea et al., "The pressures in the episcleral veins, Schlemm's canal and the trabecular meshwork in monkeys: Effects of changes in intraocular pressure", Exp. Eye Res., 49:645-663, Oct. 1989.

Nicolle et al., "A silastic tendon prothesis as an adjunct to flexor tendon grafting . . . ", British Journal of Plastic Surgery, 22(3-4):224-236, (year of pub. sufficiently earlier than effective US filing date and any foreign priority date) 1969.

Rubin et al., "The use of acellular biologic tissue patches in foot and ankle surgery", Clinics in Podiatric Medicine and Surgery, 22:533-552, Oct. 2005.

Schultz, "Canaloplasty procedure shows promise for open-ankle glaucoma in European study", Ocular Surgery News, pp. 34-35, Mar. 1, 2007.

Spiegel et al., "Schlemm's canal implant: A new method to lower intraocular pressure in patients with POAG", Ophthalmic Surgery and Lasers, 30(6):492-494, Jun. 1999.

Stetson et al., "Arthroscopic treatment of partial rotator cuff tears", Operative Techniques in Sports Medicine, 12(2):135-148, Apr. 2004.

Valdez et al., "Repair of digital flexor tendon lacerations in the horse, using carbon fiber implants", JAYMA, 177(5):427-435, Sep. 1, 1980.

"Rotator cuff tear", Wikipedia, the free encyclopedia, downloaded from <http://en.wikipedia.org/wiki/Roatator_cuff_tear> on Dec. 6, 2012, 14 pages.

Euteneuer et al., U.S. Appl. No. 13/717,474 entitled "Apparatus and Method for Forming Pilot Holes in Bone and Delivering Fasteners Therein for Retaining an Implant," filed Dec. 17, 2012.

Euteneuer et al., U.S. Appl. No. 13/717,493 entitled "Fasteners and Fastener Delivery Devices for Affixing Sheet-Like Materials to Bone or Tissue," filed Dec. 17, 2012.

All non-patent literature documents and foreign patent documents have been previously uploaded in parent U.S. Appl. No. 12/684,774, filed Jan. 8, 2010; U.S. Appl. No. 13/763,414, filed Feb. 8, 2013.

\* cited by examiner

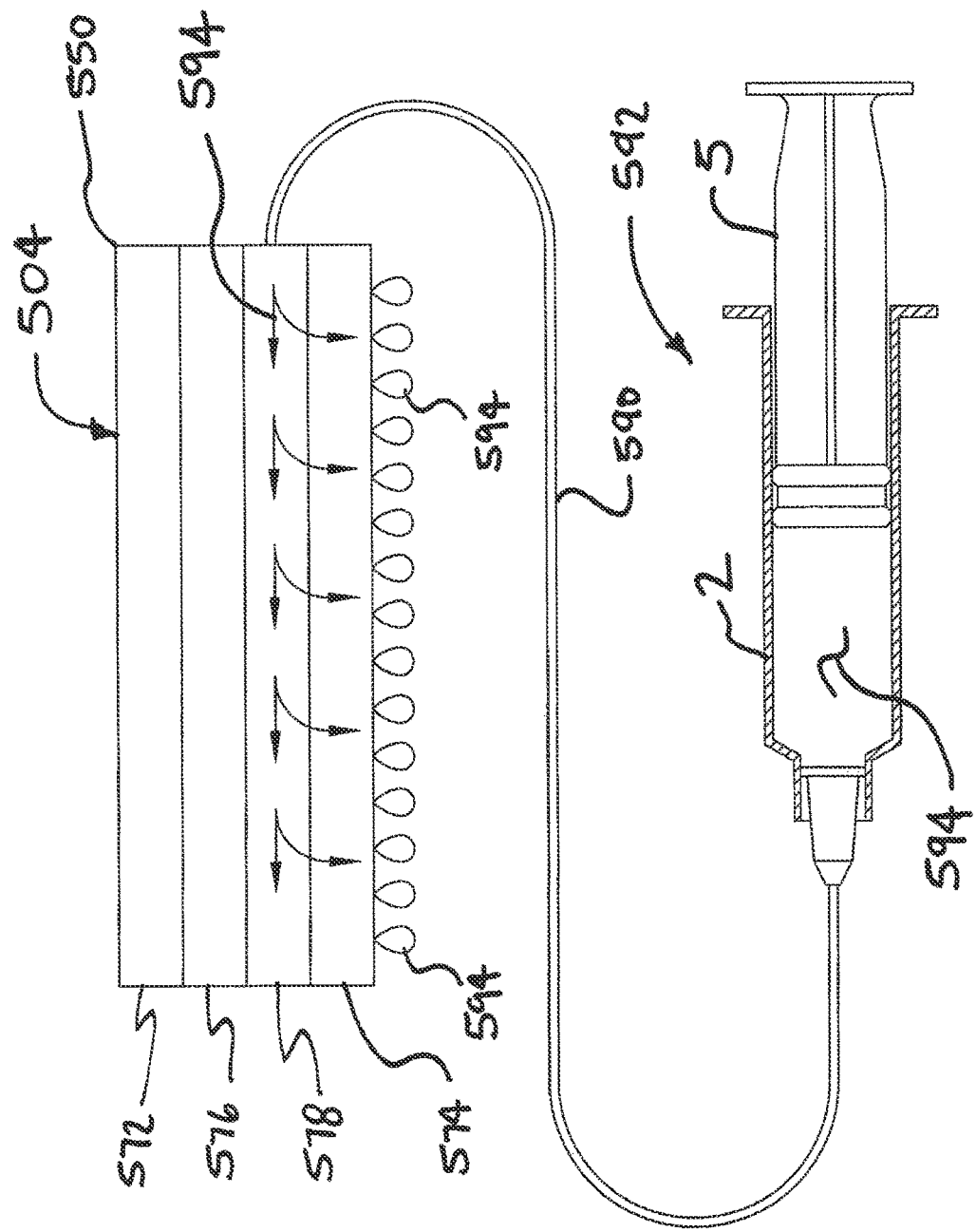

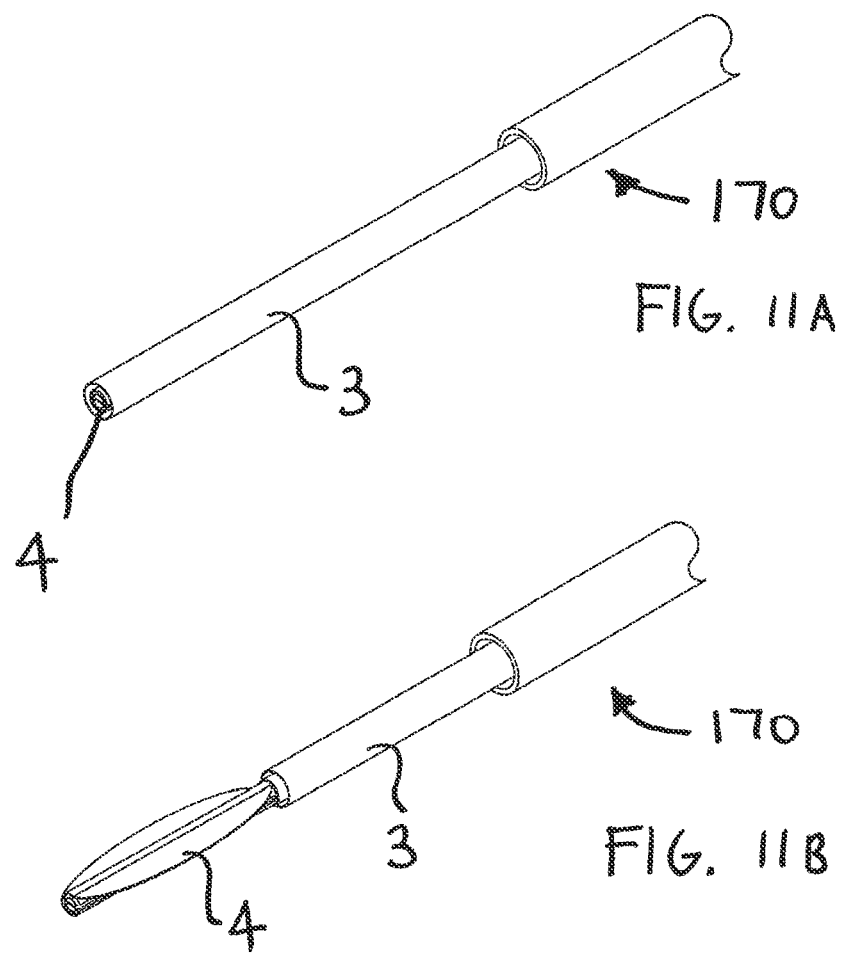
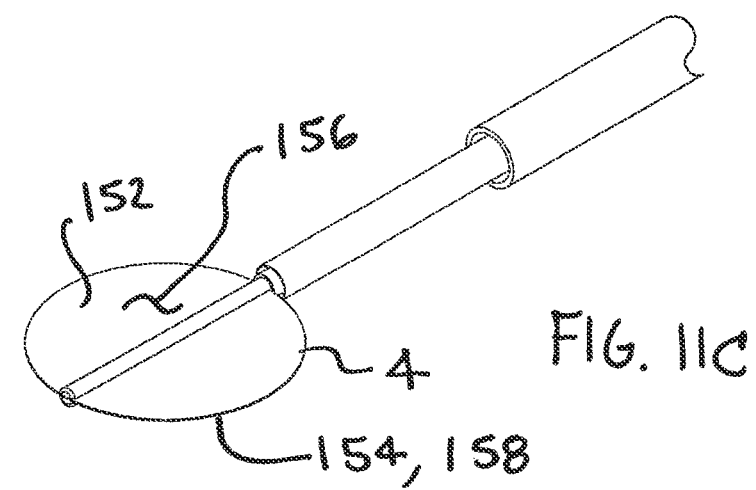

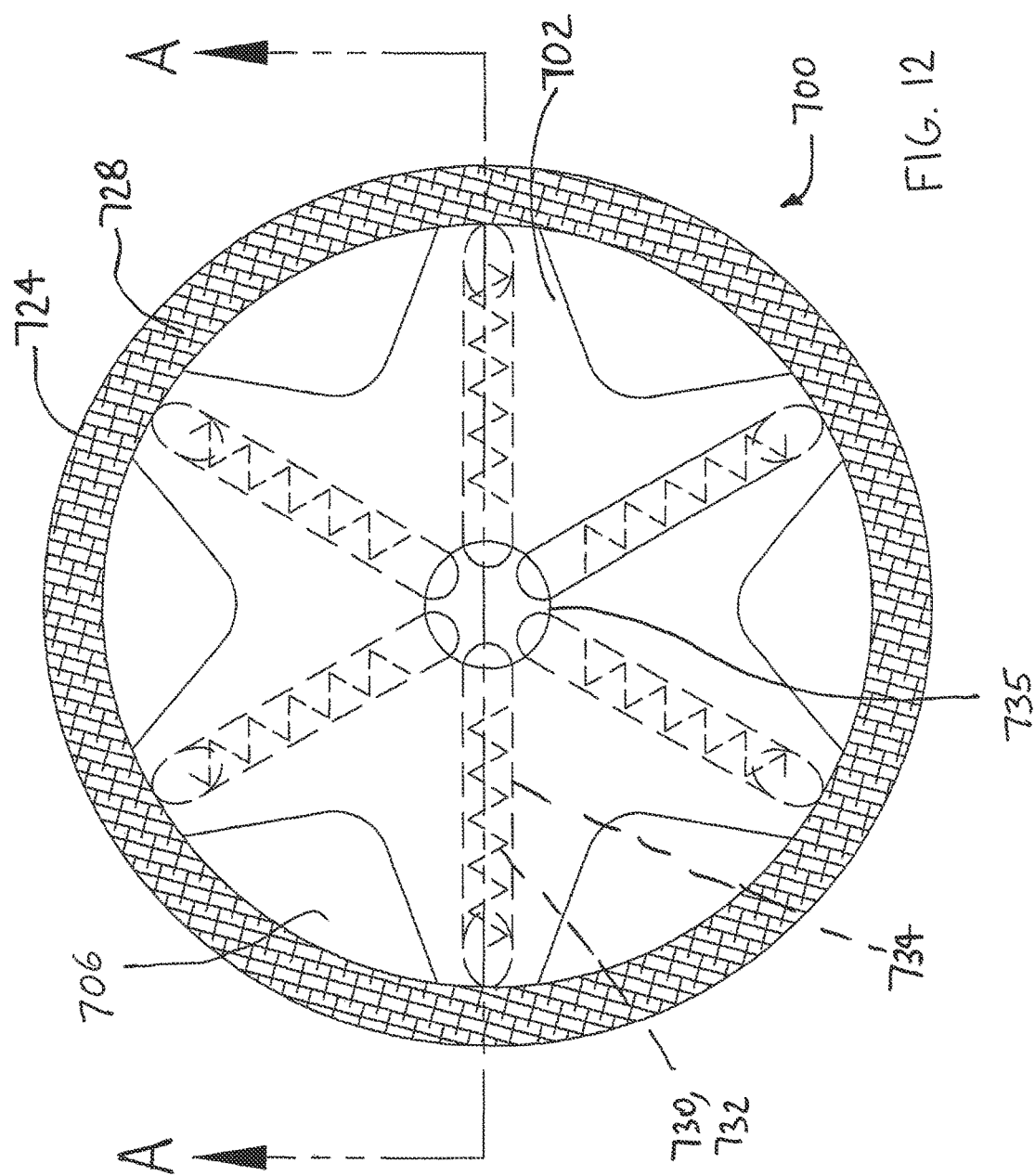

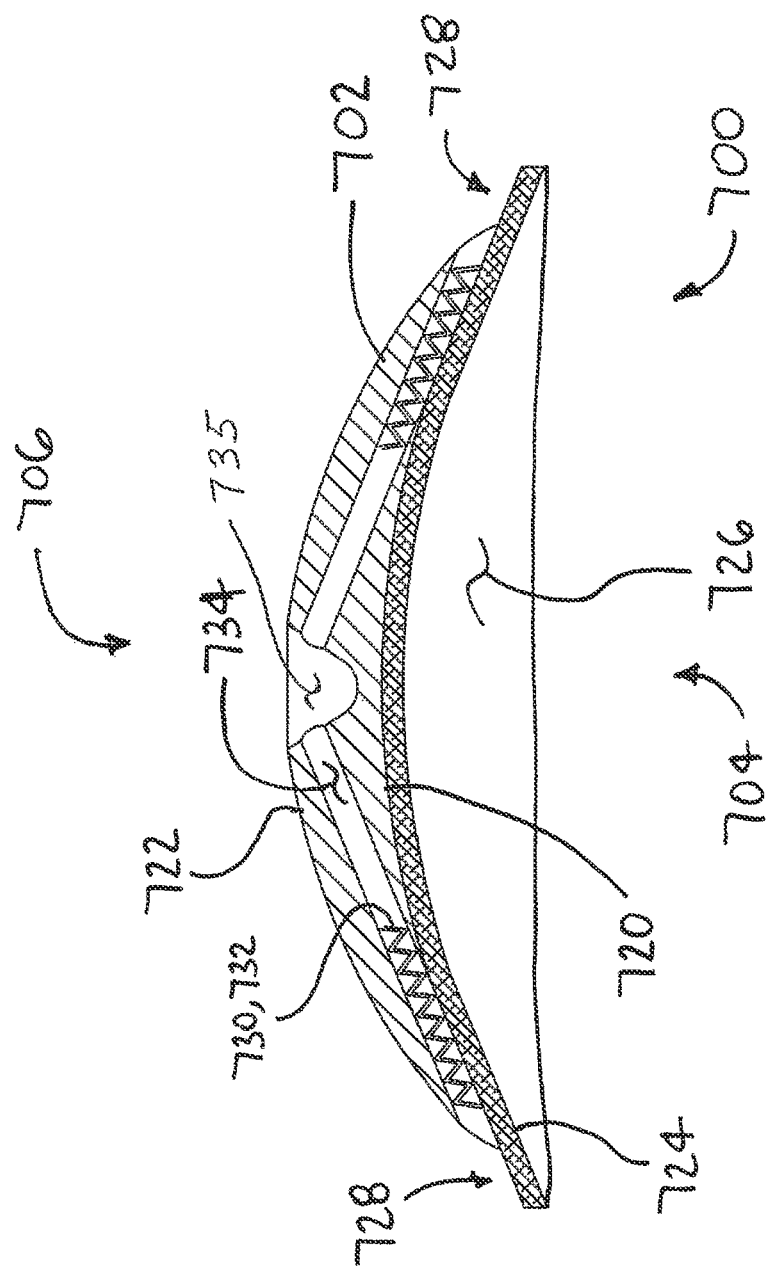

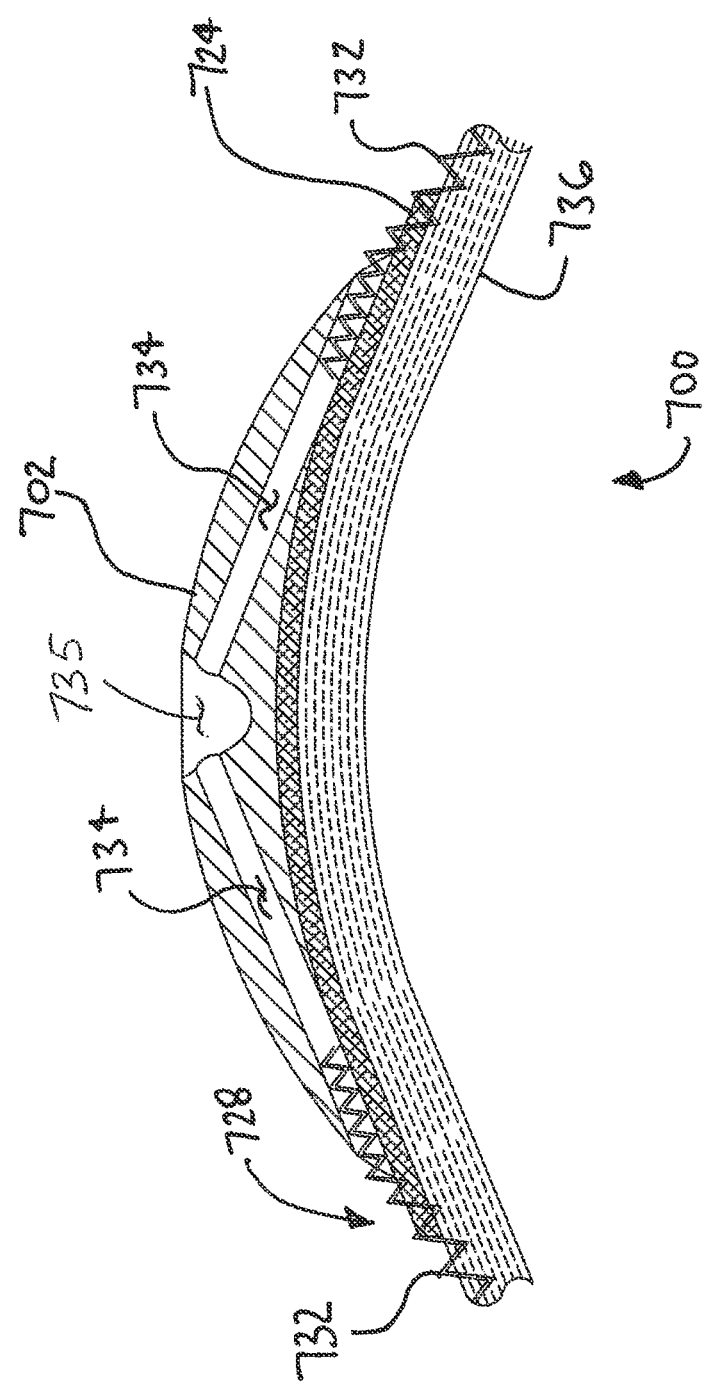

IMPLANTABLE TENDON PROTECTION SYSTEMS AND RELATED KITS AND METHODS

CROSS REFERENCE TO RELATED APPLICATIONS

This application is a continuation of U.S. application Ser. No. 13/763,414, filed on Feb. 8, 2013, which is a continuation of U.S. application Ser. No. 12/684,774, filed on Jan. 8, 2010, which claims the benefit of U.S. Provisional Application No. 61/253,800, filed on Oct. 21, 2009; 61/184,198 filed on Jun. 4, 2009; 61/162,234 filed Mar. 20, 2009; 61/153,592 filed on Feb. 18, 2009, and 61/143,267 filed on Jan. 8, 2009, the disclosures of each incorporated herein by reference.

FIELD

The present invention relates generally to orthopedic medicine and surgery. More particularly, the present invention relates to methods and apparatus for delivery and fixation of sheet-like implants, such as for treating articulating joints.

BACKGROUND

Injuries to soft tissue, including, for example, musculoskeletal tissue, may require repair by surgical intervention, depending upon factors such as the severity and type of injury. Such surgical repairs can be effected by using a number of conventional surgical procedures, for example, by suturing the damaged tissue, and/or by mounting an implant to the damaged tissue. It is known that an implant may provide structural support to the damaged tissue, and it may also serve as a substrate upon which cells can grow, thus facilitating more rapid healing.

One example of a fairly common soft tissue injury is damage to the rotator cuff or rotator cuff tendons. The rotator cuff facilitates circular motion of the humerus relative to the scapula. Damage to the rotator cuff is a potentially serious medical condition that may occur during hyperextension, from an acute traumatic tear or from overuse of the joint. The most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury. Additionally, the strain or tear can occur within the tendon itself. Treatment for a strained tendon usually involves physical cessation from use of the tendon, i.e., rest. However, depending upon the severity of the injury, a torn tendon might require surgical intervention as in the case of a full tear or detachment of the supraspinatus tendon from the humerus. Such surgical interventions include debridement, acromioplasty, and various procedures for reconnecting tendons to bone or strengthening damaged tendon to bone connections. Damage to the rotator cuff may also include degeneration. This is a common situation that arises in elderly patients. In degenerative cases there is loss of the superior portion of the rotator cuff with complete loss of the supraspinatus tendon. Similar soft tissue pathologies include tears in the Achilles' tendon, the anterior cruciate ligament and other tendons or ligaments of the knee, wrist, hand, and hip, spine, etc.

Some studies suggest that 85% of people over the age of 65 have some degree of shoulder tendon damage. Well-established procedures exist for repairing fully torn tendons, such as rotator cuff tendons, as previously mentioned. However, adequate treatments do not currently exist for partially torn tendons. There is a large need for less invasive surgical techniques and systems for effecting tendon repair, particularly for the supraspinatus tendon.

SUMMARY OF THE DISCLOSURE

In accordance with aspects of the disclosure, an implantable tendon protection system is provided which comprises a body adapted to be implanted within a bursa overlying a tendon of a patient. The body comprising a tendon engaging surface configured to attach to the tendon. The body may further comprise a sliding surface adapted to slide with respect to the bursa. In some embodiments, the tendon engaging surface comprises adhesive. The body may be configured to be movable between a collapsed state in which the body may be received within a cannula cavity, and a deployed state in which the body may extend across an interior portion of the bursa. In some embodiments, the body is configured to attach to a partially torn tendon. The body may comprise a middle portion that is less flexible than an edge portion.

In some of the above embodiments, the body is constructed from individual layers. A first layer may comprise a sliding surface and a second layer may comprise a tendon engaging surface, a mesh material, a plurality of fibers, and/or a bioabsorbable material. One or more intermediate layers may be located at least partially between the first and second layers. In some embodiments, a cushioning layer is interposed between the first and second layers. An intermediate layer may comprise at least one channel which may fluidly communicate with the tendon engaging surface. In some embodiments the sliding surface has a lower coefficient of friction than that of the tendon engaging surface.

In accordance with other aspects of the disclosure, a surgical kit is provided which comprises a system such as described above and an insertion cannula. The insertion cannula may include a portion configured to enter a body of a patient. This portion includes a cavity for receiving the system when in a collapsed state. The insertion cannula may further comprise a mechanism configured to remove the system from the cavity when the insertion cannula portion is within the body of the patient. The removal mechanism may comprise a push rod at least partially located within the insertion cannula and movable along a longitudinal axis of the insertion cannula.

In accordance with other aspects of the disclosure, methods of protecting a tendon of a patient are disclosed. In some embodiments, the method includes the steps of inserting a device into an at least partially viable bursa of the patient to a position overlying the tendon, and engaging a first surface of the implant with the tendon. The method may further include the step of attaching the device to the tendon. In some embodiments, the attaching step comprises the use of an adhesive. The adhesive may be urged through a channel in the device when the device is positioned within the body of the patient. In some embodiments, the inserting step comprises at least partially receiving the device within a portion of an insertion instrument, inserting the portion of the insertion instrument into the body of the patient, and removing the device from the insertion instrument while the portion is within the body. The device may be caused to assume the deployed state at least partially by introducing a fluid into an inflatable portion of the device.

In some embodiments, the above methods may further comprise the step of delivering a therapeutic or diagnostic agent to tissue adjacent the device. The therapeutic or diagnostic agent may include a drug, anti-inflammatory agent, painkiller, antibiotic, protein, and/or a hormone.

In some embodiments, a second surface of the device is deployed to slide relative to the bursa. The device may serve to protect a damaged portion of the tendons. In some embodiments, the device does not substantially reinforce the engaged tendons by transmitting a significant load of the tendons. The device may serve to remove a stimulus from nerves in the engaged tendons. The removed stimulus may include one or more of pressure, temperature, chemical, electrical and inflammation stimulus. In some embodiments the device is not sutured to the tendons or other tissue. The inserting step may comprise the use of an arthroscopic instrument. In some embodiments the tendon comprises a partially torn tendon. The attaching step may comprise securing the device to the tendon using a plurality of anchors.

In accordance with other aspects of the disclosure, a method is provided which comprises identifying a partially torn portion of a tendon and covering the partially torn portion of the tendon. In some embodiments a device may be positioned over the partially torn portion of the tendon and fixed to the tendon. The device may be fixed to the tendon with adhesive, sutures, staples, and/or anchors. Covering the partially torn portion of the tendon may spread impinging forces across a surface area of the device. In some embodiments a therapeutic agent that promotes growth of tissue into pores defined by the device may be delivered. The therapeutic agent may promote encapsulation of the device within a cellular encapsulation layer. The therapeutic agent may induce the growth of synovial cells on an outer surface of the device. The therapeutic agent may induce the growth of bursa cells on an outer surface of the device. The therapeutic agent may desensitize stimulated nerve receptors proximate the partially torn portion of the tendon. The therapeutic agent may promote the growth of a cellular encapsulation barrier over the partially torn portion of the tendon.

In some embodiments, covering the partially torn portion of the tendon inhibits the partially torn portion of the tendon from becoming a tear extending through a total thickness of the tendon. Covering the partially torn portion of the tendon may inhibit physical stimulus of the partially torn portion by adjacent tissues. Covering the partially torn portion of the tendon may protect damaged tendon fibers from mechanical agitation by adjoining tissues. Covering the partially torn portion of the tendon may alleviate pain, which in turn may restore shoulder function. In some embodiments, covering the partially torn portion of the tendon protects the partially torn portion of the tendon. Covering the partially torn portion of the tendon may prevent abrasion of the partially torn portion of the tendon. Covering the partially torn portion of the tendon may reduce friction between the partially torn portion of the tendon and adjacent tissues. Covering the partially torn portion of the tendon may cushion forces applied to the partially torn portion of the tendon by adjacent tissues.

BRIEF DESCRIPTION OF THE DRAWINGS

FIG. 10 is a stylized block diagram illustrating an exemplary implantable device coupled to a syringe.

FIGS. 11A, 11B, and 11C are a series of isometric views illustrating the deployment of an exemplary implantable device.

FIG. 12 is a plan view illustrating an exemplary implantable device.

FIG. 13 is a side cross-sectional view taken along line A-A in FIG. 12.

FIG. 14 is a side cross-sectional view taken along line A-A in FIG. 12 and illustrating the device of FIG. 12 anchored to a tendon.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
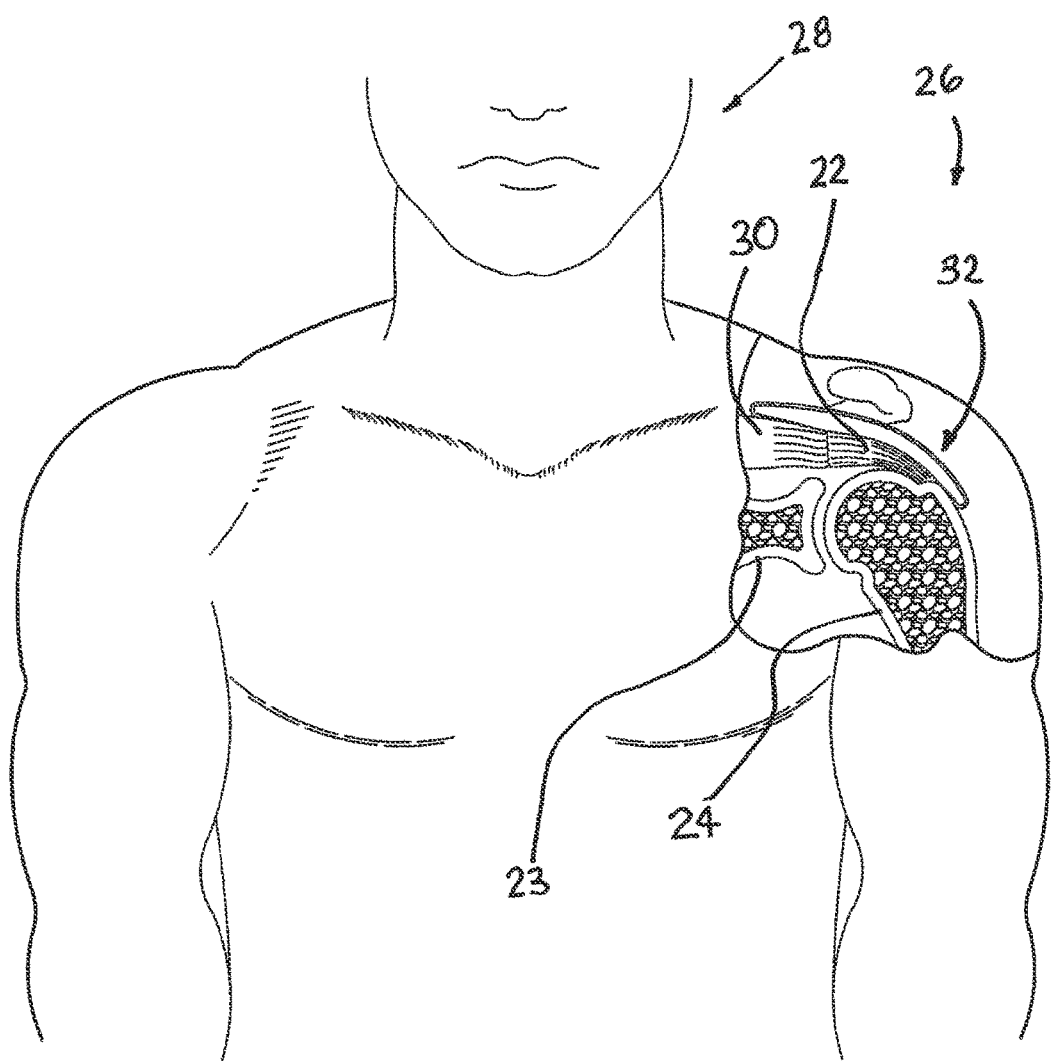
FIG. 1 is an anterior view showing the upper torso of a patient with the left shoulder shown in cross-section.

FIG. 1 is a stylized anterior view of a patient 28. For purposes of illustration, a shoulder 26 of patient 28 is shown in cross-section in FIG. 1. Shoulder 26 includes a humerus 24 and a scapula 23. The movement of humerus 24 relative to scapula 23 is controlled by a number of muscles including: the deltoid, the supraspinatus, the infraspinatus, the subscapularis, and the teres minor. For purposes of illustration, only the supraspinatus 30 is shown in FIG. 1. With reference to FIG. 1, it will be appreciated that a distal tendon 22 of the supraspinatus 30 meets humerus 24 at an insertion point 32.

Figure 2:
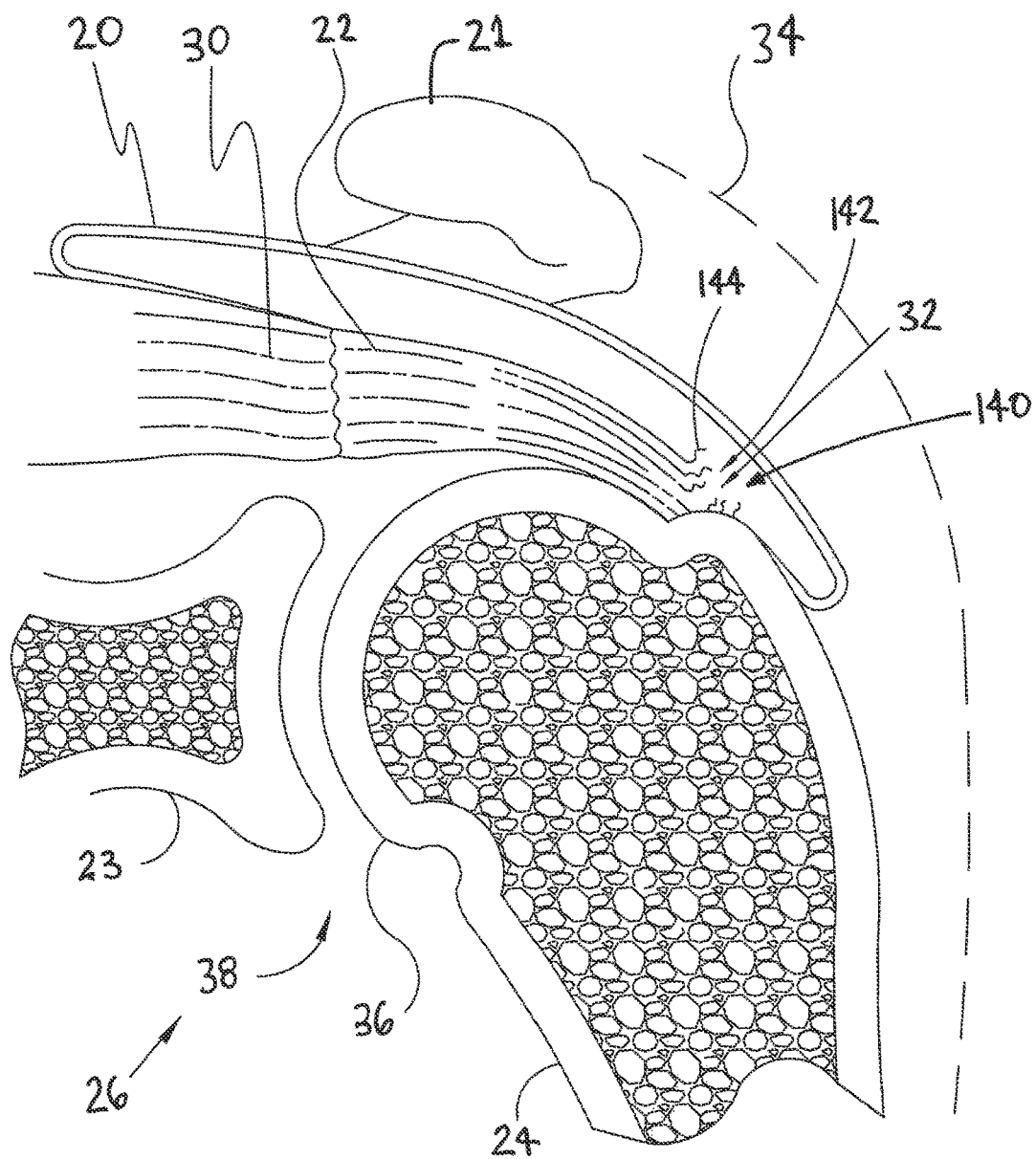
FIG. 2 is an enlarged, cross-sectional view showing the left shoulder depicted in FIG. 1.

FIG. 2 is an enlarged cross sectional view of shoulder 26 shown in the previous figure. In FIG. 2, a head 36 of humerus 24 is shown mating with a glenoid fossa of scapula 23 at a glenohumeral joint 38. The glenoid fossa comprises a shallow depression in scapula 23. A supraspinatus 30 and a deltoid 34 are also shown in FIG. 2. These muscles (along with others) control the movement of humerus 24 relative to scapula 23.

A distal tendon 22 of supraspinatus 30 meets humerus 24 at an insertion point 32. In the embodiment of FIG. 2, tendon 22 includes a damaged portion 140 located near insertion point 32. Damaged portion 140 includes a tear 142 extending partially through tendon 22. Tear 142 may be referred to as a partial thickness tear. Tendon 22 of FIG. 2 has become frayed. A number of loose tendon fibers 144 are visible in FIG. 2.

Scapula 23 includes an acromium 21. In FIG. 2, a subacromial bursa 20 is shown extending between acromium 21 of scapula 23 and head 36 of humerus 24. In FIG.

2, subacromial bursa 20 is shown overlaying supraspinatus 30. Subacromial bursa 20 is one of more than 150 bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

Figure 3:
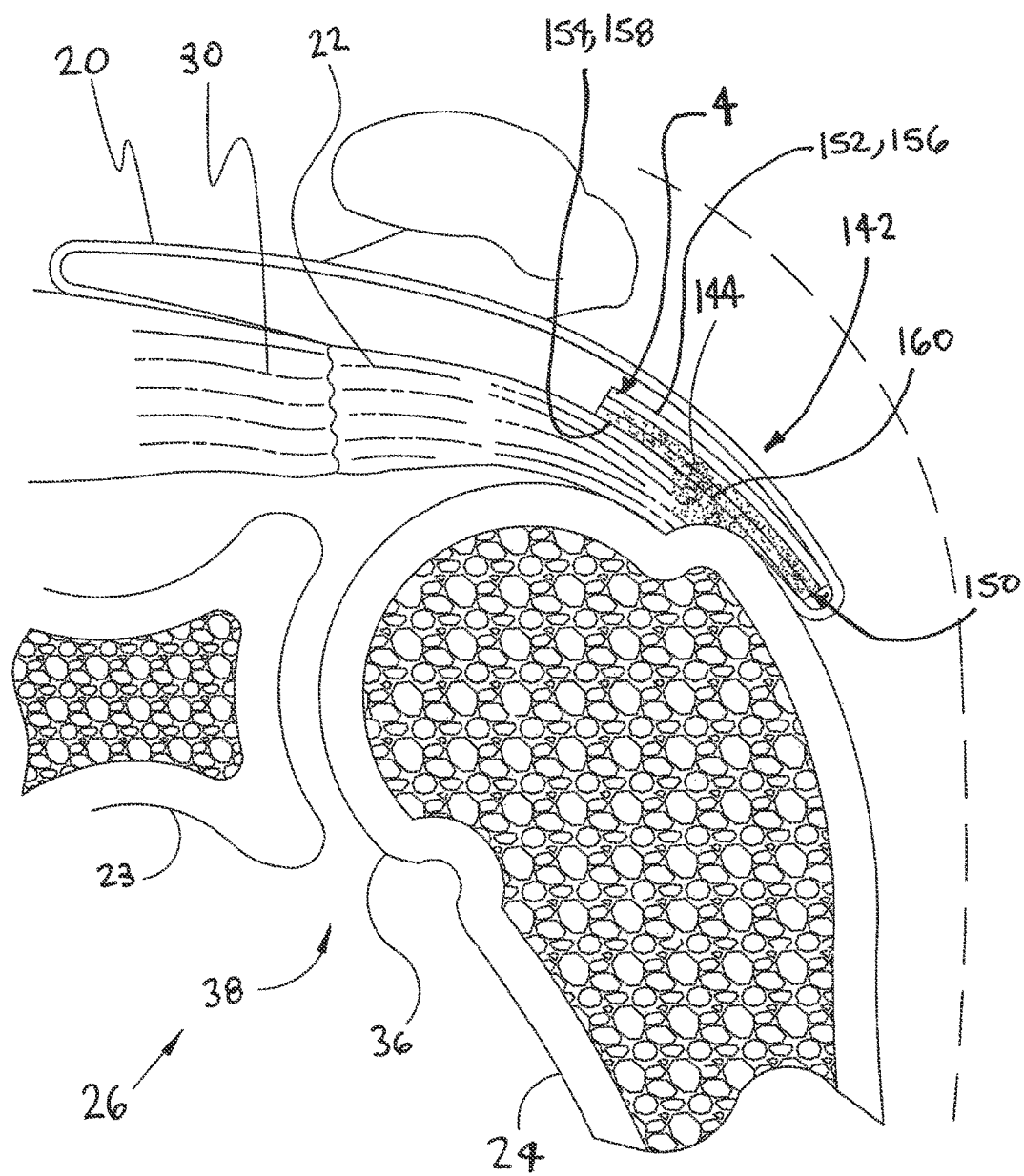
FIG. 3 is an enlarged, cross-sectional view showing an exemplary implantable device in accordance with aspects of the invention inserted into the shoulder.

FIG. 3 is an additional cross sectional view of shoulder 26 shown in the previous figure. In the embodiment of FIG. 3, a device 4 has been implanted inside subacromial bursa 20. Device 4 comprises a body 150. Body 150 is adapted to be implanted within a bursa overlaying a tendon of a patient.

In FIG. 3, body 150 of device 4 is shown overlaying tear 142. In the exemplary embodiment of FIG. 3, body 150 comprises a first side 152 and a second side 154. First side 152 comprises a sliding surface 156 and second side 154 comprises a tendon engaging surface 158. Sliding surface 156 is adapted to slide with respect to adjacent tissues (e.g., bursa tissue). Tendon engaging surface 158 is configured to attach to a tendon.

In the exemplary embodiment of FIG. 3, fibers 144 of tendon 22 are fixed to device 4 by an adhesive 160. Adhesive 160 is illustrated using dots in FIG. 3. With reference to FIG. 3, it will be appreciated that adhesive 160 permeates a portion of device 4. Some exemplary methods in accordance with the present detailed description include injecting an adhesive into channels defined by a device so that the adhesive exits a plurality of apertures defined by a tissue engaging layer of the device. The adhesive may elute over a large area to affix the device to a tendon. Some additional exemplary methods in accordance with the present detailed description include injecting a therapeutic agent (e.g., a drug) into channels defined by a device so that the therapeutic agent exits a plurality of apertures defined by a tissue engaging layer of the device.

Figure 4:
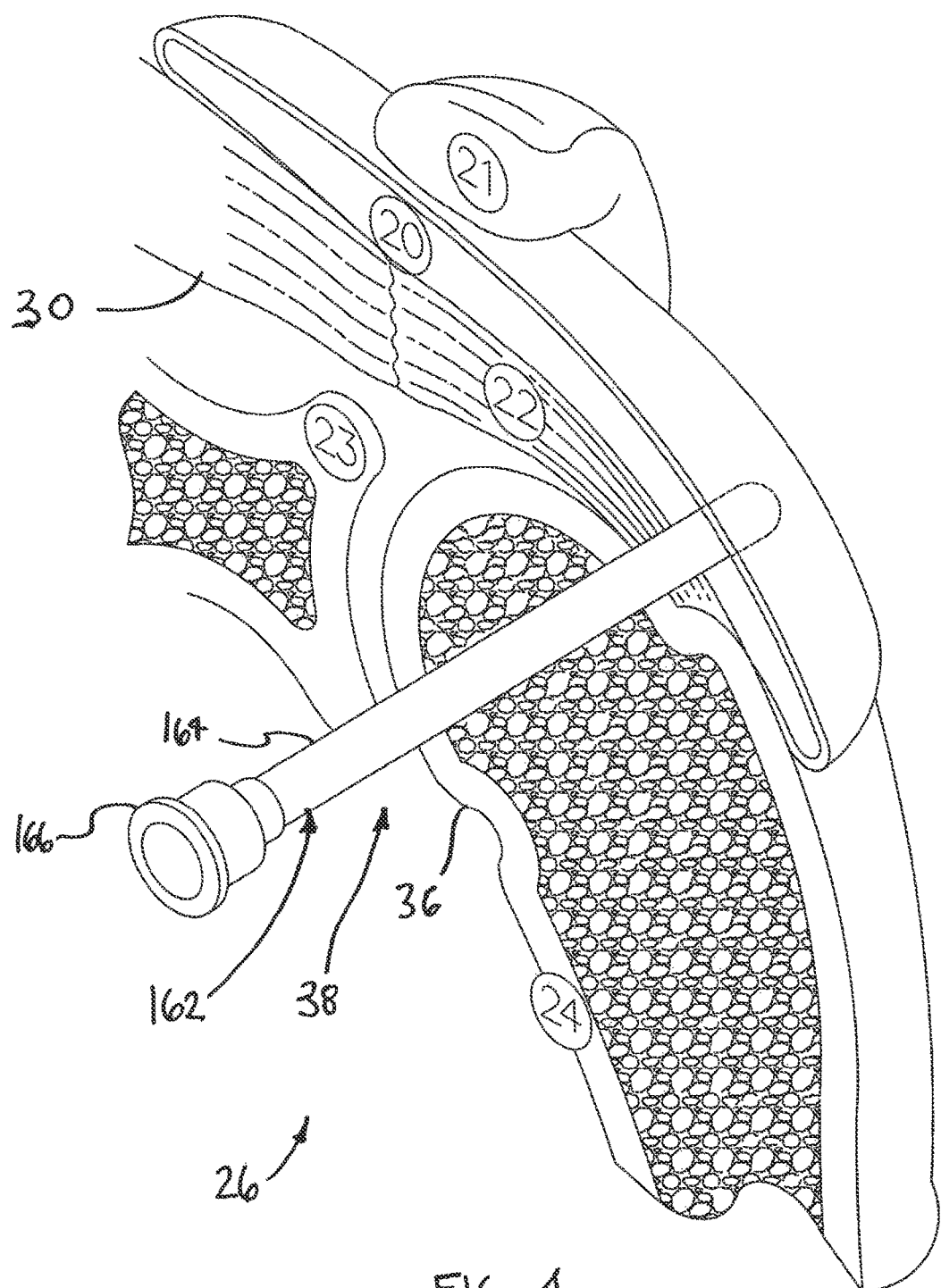
FIG. 4 is an enlarged, oblique, cross-sectional view showing an exemplary cannula inserted into the bursa of the shoulder.

FIG. 4 is an isometric view of a shoulder 26. Shoulder 26 includes a humerus 24 and a scapula 23. Humerus 24 comprises a head 36 having a generally spherical surface. Head 36 of humerus 24 mates with a shallow depression defined by the scapula 23 at a glenohumeral joint 38. In FIG. 4, a distal tendon 22 of a supraspinatus 30 is shown meeting humerus 24 at an insertion point. Supraspinatus 30 (along with a number of other muscles) controls the movement of humerus 24 relative to scapula 23.

In FIG. 4, a subacromial bursa 20 is shown overlaying a portion of supraspinatus 30. Subacromial bursa 20 comprises a fluid filled sac that acts to reduce friction between tissues in the body. In FIG. 4, subacromial bursa 20 is shown extending between a portion of supraspinatus 30 and an acromium 21 of scapula 23. In the embodiment of FIG. 4, the distal end of a cannula 162 has been inserted into the interior of bursa 20. Cannula 162 may be inserted, for example, near a site where tendon damage exists. Cannula 162 includes a shaft 164 defining a lumen and a hub 166 that is fixed to a proximal end of shaft 164. In the embodiment of FIG. 4, the lumen defined by cannula 162 fluidly communicates with an interior of subacromial bursa 20. Accordingly, a device may be placed in the interior of subacromial bursa 20 by advancing that device through the lumen defined by cannula 162.

Figure 5:
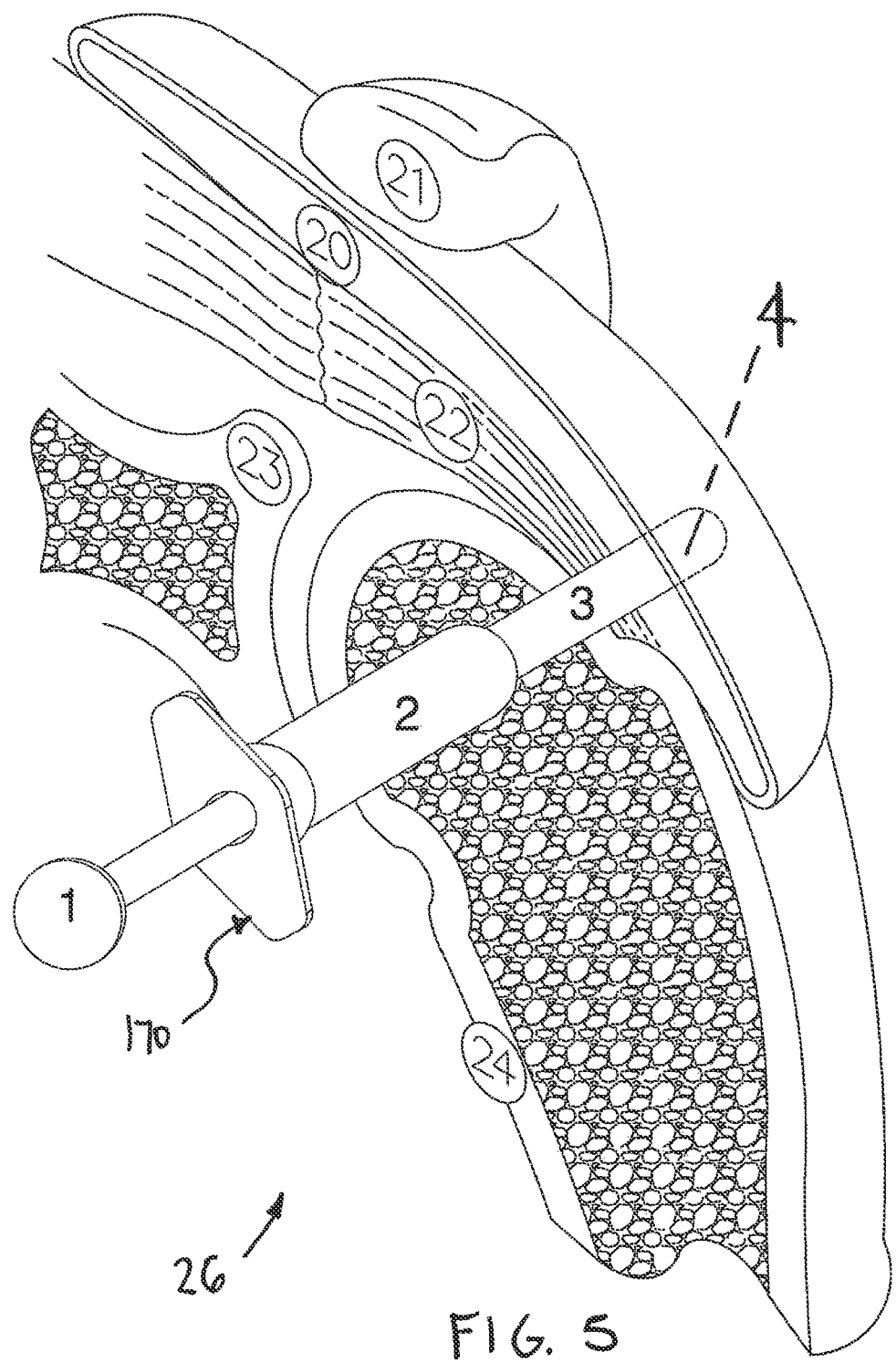
FIG. 5 is an enlarged, oblique, cross-sectional view showing an exemplary delivery system inserted into the shoulder.

FIG. 5 is an additional isometric view of shoulder 26 shown in the previous figure. A delivery system 170 is shown in FIG. 5. Delivery system 170 of FIG. 5 comprises a sheath 3, a barrel 2, and a plunger 1. In the embodiment of FIG. 5, a device 4 is disposed inside sheath 3. Some methods in accordance with the present detailed description may include the step of causing the body of a device to assume a collapsed shape and inserting the body of the device into a sheath. The sheath and the body of the device may both be inserted into a bursa. Once inside the bursa, the body may assume a deployed shape.

It is to be appreciated that the length of delivery system 170 may vary from that shown in FIG. 5 without deviating from the spirit and scope of the present detailed description. In useful some embodiments, a portion of delivery system 170 may extend through a cannula (e.g., the cannula shown in the previous figure). The cannula may guide the distal end of delivery system 170 to a target site.

Figure 6:
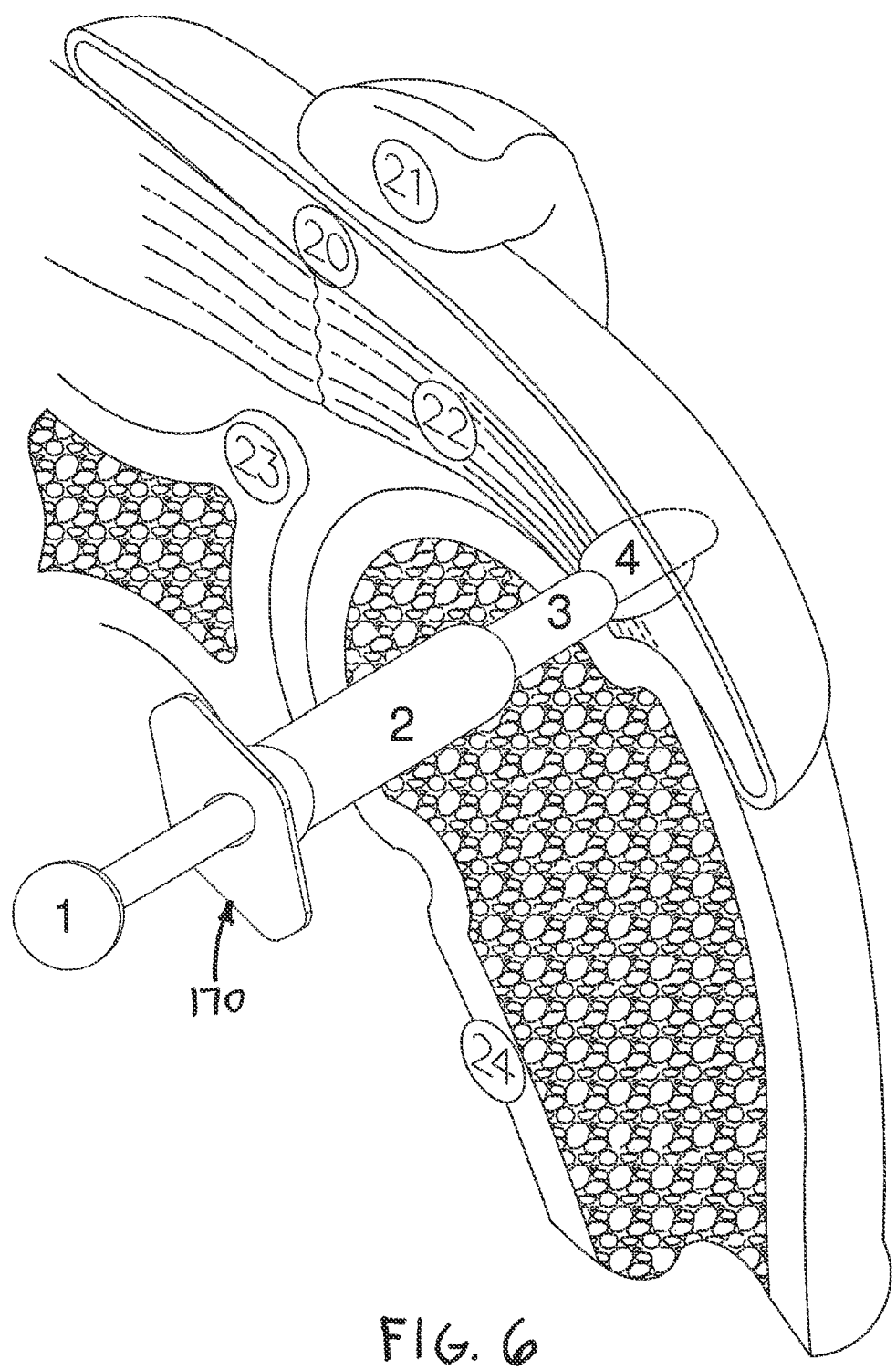
FIG. 6 shows the delivery system of FIG. 5 with the sheath retracted.

FIG. 6 is an additional isometric view showing delivery system 170 shown in the previous figure. In the embodiment of FIG. 6, sheath 3 of delivery system 170 has been retracted from device 4, exposing device 4. In other embodiments, sheath 3 may remain stationary while device 4 is extended from within the sheath, or device 4 may be deployed with a combination of movements of the sheath and the device. In some useful embodiments, device 4 assumes a generally cylindrical shape while disposed inside sheath 3. In the embodiment of FIG. 6, deployment of device 4 has been initiated. Accordingly, device 4 is shown assuming a somewhat enlarged shape in FIG. 6.

Figure 7:
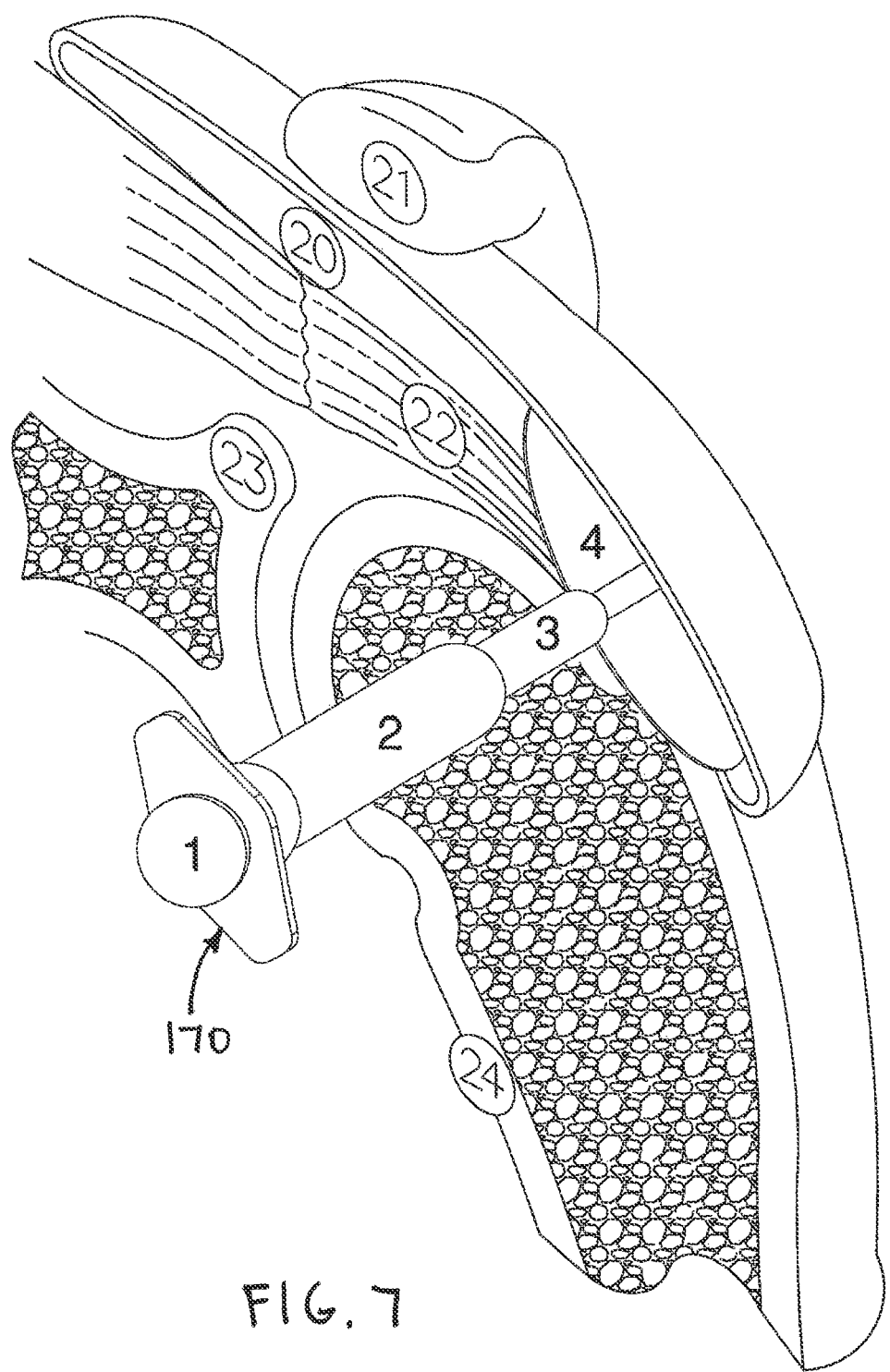
FIG. 7 shows the delivery system of FIG. 5 with the implantable device completely deployed.

FIG. 7 is an additional isometric view showing delivery system 170 shown in the previous figure. In FIG. 7, device 4 is shown assuming a completely deployed shape. In the exemplary embodiment of FIG. 7, device 4 is generally plate-shaped and circular when fully deployed. In some advantageous embodiments, the body of device 4 is flexible.

Some exemplary methods in accordance with the present detailed description include injecting an adhesive into channels defined by a device so that the adhesive exits a plurality of apertures defined by a tissue engaging layer of the device. The adhesive may elute over a large area to affix the device to a tendon. Delivery system 170 may be withdrawn from shoulder 26 after the delivery of device 4 is complete.

Figure 8:
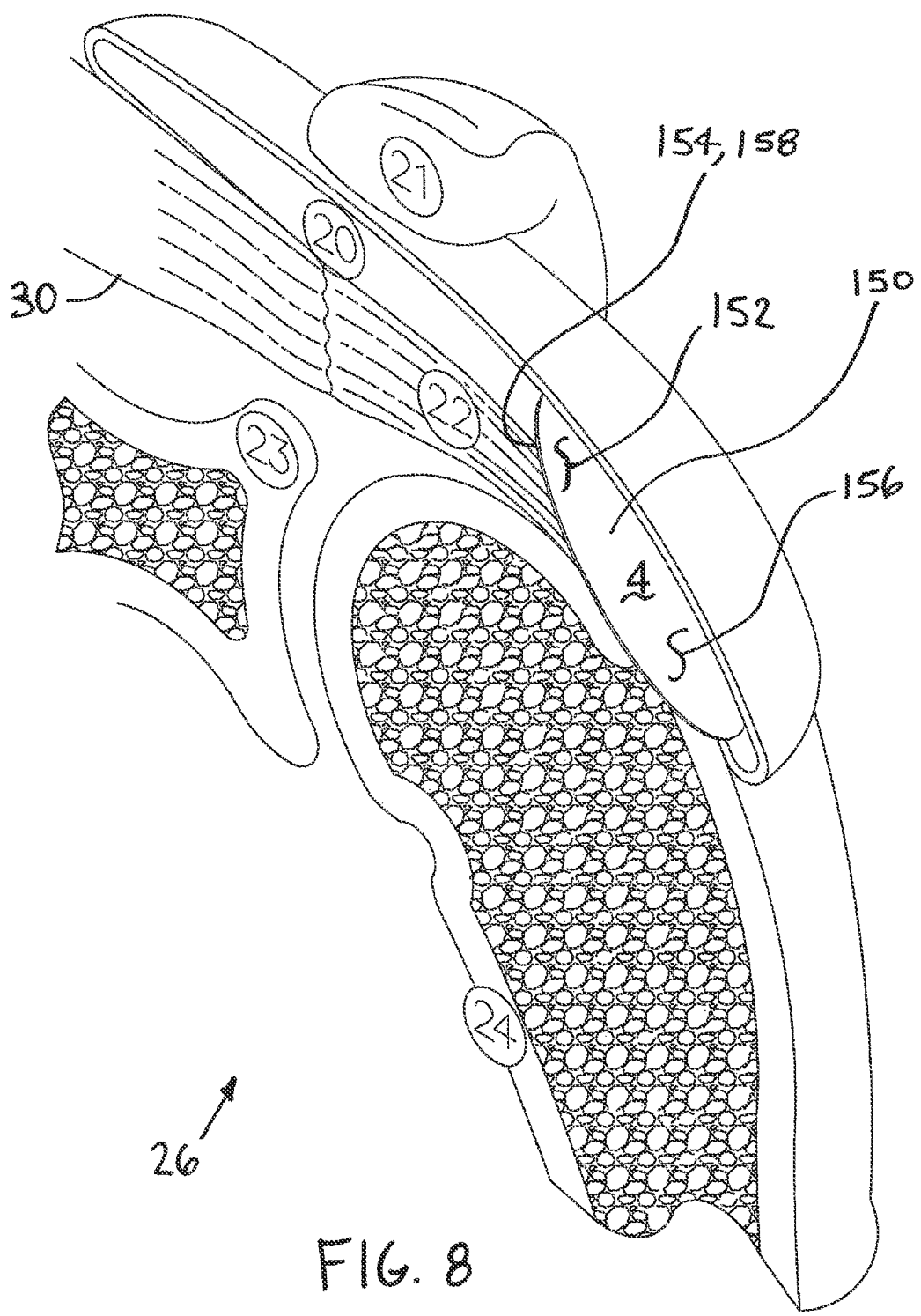
FIG. 8 shows the implantable device in place with the delivery system of FIG. 5 removed.

FIG. 8 is an additional cross sectional view of shoulder 26 shown in the previous figure. In the embodiment of FIG. 8, device 4 has been implanted inside subacromial bursa 20. In FIG. 8, device 4 is shown overlaying a portion of distal tendon 22 of supraspinatus 30. In the exemplary embodiment of FIG. 8, device 4 comprises a body 150 having a first side 152 and a second side 154. First side 152 comprises a sliding surface 156 and second side 154 comprises a tendon engaging surface 158. In the embodiment of FIG. 8, body 150 has been positioned so that tendon engaging surface 158 engages tendon 22. Tendon engaging surface 158 may be fixed to distal tendon 22, for example, with an adhesive. When device 4 is overlaying tendon 22 as shown in FIG. 8, device 4 provides a sliding surface 156 facing away from tendon 22.

Figure 9:
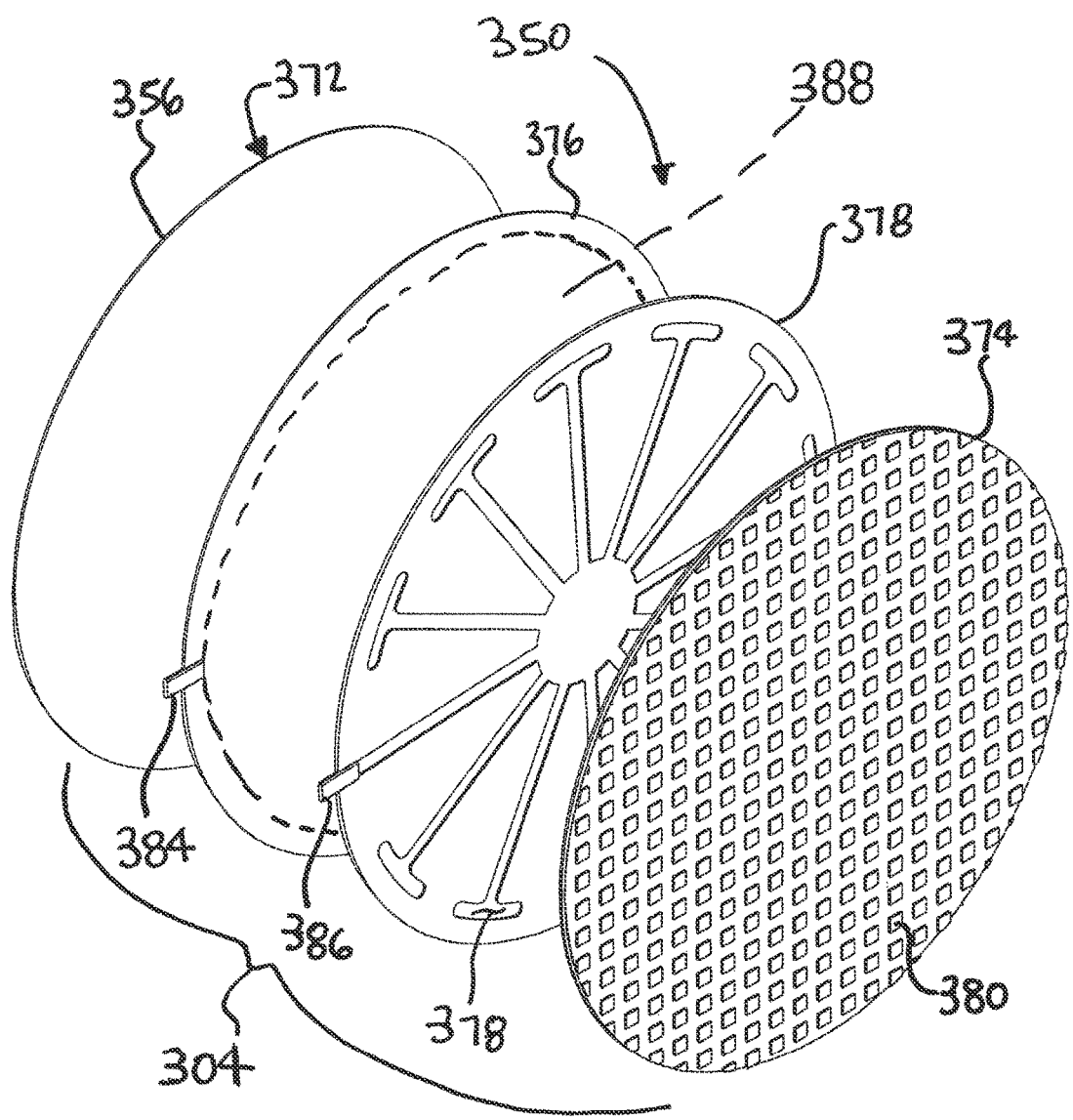
FIG. 9 is an exploded isometric view illustrating an exemplary implantable device.

FIG. 9 is an exploded isometric view illustrating an exemplary device 304 in accordance with the present detailed description. In the exemplary embodiment of FIG. 9, device 304 comprises a body 350 including a first layer 372, a second layer 374, a first intermediate layer 376, and a second intermediate layer 378.

When device 304 is overlaying tendon 22, first layer 372 of device 304 provides a sliding surface 356 facing away from the tendon. In the exemplary embodiment of FIG. 9, second layer 374 comprises a biocompatible material for use against the tendon surface. In the embodiment of FIG. 9, second layer 374 defines a plurality of apertures 380. In one exemplary embodiment, second layer 374 comprises a mesh material. In some embodiments, second layer 374 may comprise a plurality of fibers. The fibers may be interlinked with one another. When this is the case, second layer 374 may comprise a plurality of apertures comprising the interstitial spaces between fibers. Various processes may be used to interlink the fibers with one another. Examples of processes that may be suitable in some applications including weaving, knitting, and braiding.

In some useful embodiments, second layer 374 comprises one or more bioabsorbable materials. Examples of bioabsorbable materials that may be suitable in some applications include those in the following list, which is not exhaustive: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), poly(alpha-hydroxy acid) or related copolymers materials.

In the exemplary embodiment of FIG. 9, second intermediate layer 378 comprises a plate defining a plurality of channels. Channels 382 of second intermediate layer 378 and apertures 380 of second layer 374 may allow a fluid to elute over a large area to device 304 to a tendon. Second intermediate layer 378 may also distribute stresses across device 304. When pressure from adjacent tissues is applied to device 304, the device will spread that pressure across an area of a tendon covered by device 304. This function helps device 304 to reduce stimulus to nerves in the covered tendon.

A second inlet 386 is visible in FIG. 9. An interior of second inlet 386 is in fluid communication with channels 382 of second intermediate layer 378. When device 304 is in an assembled state, channels 382 fluidly communicate with apertures 380 defined by second layer 374. Fluid may be injecting into channels 382 and through apertures 380 by injecting the fluid into second inlet 386. In one method in accordance with the present detailed description, an adhesive fluid is injected into channels 382. The adhesive fluid may elute over a tissue engaging area of device 304 to affix device 304 to a tendon.

In the exemplary embodiment of FIG. 9, first intermediate layer 376 comprises a plurality of sheets defining a cavity 388. Various fluids may be injected into cavity 388. Some exemplary methods in accordance with the present detailed description may include changing the shape of shape of device 304. The shape of device 304 may be changed, for example, by injecting fluid into cavity 388. A first inlet 384 is shown in FIG. 9. An interior of first inlet 384 is in fluid communication with cavity 388 of first intermediate layer 376. Fluid may be injected into cavity 388 by injecting the fluid into first inlet 384.

FIG. 10 is a stylized block diagram illustrating an exemplary device 504 in accordance with the present detailed description. In the exemplary embodiment of FIG. 10, device 504 comprises a body 550 including a first layer 572, a second layer 574, a first intermediate layer 576, and a second intermediate layer 578.

In the embodiment of FIG. 10, second intermediate layer 578 comprises a plurality of flow channels. A tube 590 defines a lumen that is in fluid communication with the flow channels of intermediate layer. In the embodiment of FIG. 10, a proximal end of tube 590 is coupled to a syringe 592. Syringe 592 comprising a barrel 2 and a plunger 5. A fluid 594 is disposed in barrel 2. Plunger 5 of syringe 592 is capable of urging fluid 594 out of barrel 2, through tube 590, through second intermediate layer 578, and through second layer 574. The flow of fluid 594 through second intermediate layer 578 and second layer 574 is illustrated using a plurality of arrows in FIG. 10. Fluid 594 may be urged through a plurality of apertures defined by second layer 574. Fluid 594 that has exited second layer 574 is represented by a number of fluid drops in the stylized block diagram of FIG. 10.

Some exemplary methods in accordance with the present detailed description may include the step of delivering a therapeutic or diagnostic agent to tissue adjacent a device such as, for example, device 504 of FIG. 10. The fluid may comprise various therapeutic or diagnostic agents. Examples of therapeutic or diagnostic agents that may be suitable in some applications include drugs, anti-inflammatory agents, painkillers, antibiotics, proteins, and hormones.

FIGS. 11A, 11B, and 11C are a series of isometric views illustrating the deployment of a device 4. Some methods in accordance with the present detailed description may include the step of causing the body of a device to assume a collapsed shape and inserting the body of the device into a sheath. The sheath and the body of the device may both be inserted into a bursa. Once the body is inside the bursa, the body may be urged to assume a deployed shape and/or self-deploy.

In the embodiment of FIG. 11A, device 4 is disposed inside a sheath 3 of a delivery system 170. The body of device 4 may be wrapped at least partially around itself to assume a generally collapsed shape. In some useful embodiments, the body of device 4 is capable of assuming a generally cylindrical collapsed shape while disposed inside a lumen of sheath 3. The body of device 4 may also be folded to assume a generally collapsed shape.

In the embodiment of FIG. 11B, sheath 3 has been retracted from device 4. Device 4 can be seen disposed outside of sheath 3 in FIG. 11B. In the embodiment of FIG. 11B, deployment of device 4 has been initiated. Accordingly, device 4 is shown assuming a somewhat enlarged shape in FIG. 11B.

In the embodiment of FIG. 11C, device 4 has been fully deployed. In the exemplary embodiment of FIG. 11, device 4 is generally plate shaped when fully deployed. In FIG. 4, the outer edge of device 4 is shown having a generally circular shape. In the exemplary embodiment of FIG. 11, device 4 comprises a body 150 having a first side 152 and a second side 154. First side 152 comprises a sliding surface 156 and second side 154 comprises a tendon engaging surface 158. In some useful methods, device 4 is oriented over a tendon so that tendon engaging surface 158 engages the tendon.

FIGS. 12 through 14 show an additional device 700 in accordance with the present detailed description. Device 700 may be used, for example, to cover an injured portion of a tendon. FIG. 12 is a top view of device 700. FIG. 13 is section view of device 700 taken along section line A-A shown in FIG. 12. FIG. 14 is a section view similar to FIG. 13 showing device 700 in place over tendon 736.

As best seen in FIG. 13, exemplary device 700 comprises a base 702 having a first major side 704 and a second major side 706 that is opposite first major side 704. In this embodiment, first major side 704 comprises a generally concave surface 720 and second major side 706 comprises a generally convex surface 722. A sheet 724 of device 700 may be provided to overlay first major side 704 of base 702 and generally conforms to the shape of concave surface 720.

As shown in FIG. 13, sheet 724 of device 700 defines a cavity 726. In some useful embodiments, cavity 726 is dimensioned to receive a portion of a suprapinatus tendon overlying the head of a humerus. In the exemplary embodiment of FIG. 13, cavity 726 has a generally hemispherical shape. It will be appreciated that the radius of cavity 726 may vary across cavity 726 without deviating from the spirit and scope of the present description. With reference to the figures, it will be appreciated that a skirt portion 728 of sheet 724 extends beyond base 702 in this embodiment.

In some useful embodiments, sheet 724 comprises a material defining a plurality of pores that encourage tissue growth therein. A coating that encourages tissue growth or ingrowth may be applied to the surfaces of sheet 724. It will be appreciated that sheet 724 may comprise various pore defining structures without deviating from the spirit and scope of the present description. In some embodiments, the sheet 724 has a pore size in the range of 150 to 200 microns. The porosity may be about 50 percent. Examples of pore defining structures that may be suitable in some applications include open cell foam structures, mesh structures, and structures comprising a plurality of fibers. In some embodiments, the fibers may be interlinked with one another. Various processes may be used to interlink the fibers with one another. Examples of processes that may be suitable in some applications include weaving, knitting, and braiding.

Device 700 includes a plurality of anchors 730. In the exemplary embodiment shown, each anchor comprises a coil 732. It will be appreciated that anchors 730 may comprise other elements without deviating from the spirit and scope of the present description. Examples of anchoring elements that may be suitable in some applications include: coils, barbs, hooks, stables, suture pads, and sutures. In the embodiment of FIG. 13, each anchor is disposed in a lumen 734 defined by base 702. Some methods in accordance with the present description may include the step of rotating anchors 730 to screw the anchors into tissue (e.g., tendon tissue) for fixing device 700 to that tissue. A flexible catheter or other suitable driver may used to rotate anchors 730. For example, a catheter (not shown) may be removably inserted into each of the lumens 734 in turn, accessing each lumen through a central recess 735 located in second major side 706 of base 702. In some embodiments, anchors 730 threadably engage with interior surfaces of lumens 734 to facilitate advancement of the anchor into tissue.

In FIG. 14, device 700 is shown overlaying a tendon 736. To place device 700 over tendon 736, device 700 may be configured to be collapsible so that it may be inserted into the body arthroscopically, similar to the previously described devices. For example, device 700 may be collapsed like an umbrella, with its lumens 734 being substantially parallel and the material between lumens 734 forming inwardly folding pleats when in the collapsed state.

In the embodiment of FIG. 14, each coil 732 is shown extending out of a lumen 734 and into tendon 736. Tendon 736 may be, for example, a supraspinatus tendon. With reference to FIG. 14, it will be appreciated that the diameter of each coil 732 has become enlarged as it exits a lumen 734. In some useful embodiments, each coil 732 is biased to assume an increased diameter as it exits a lumen 734. In FIG. 14, each coil 732 is shown extending through a skirt portion 728 of sheet 724 that extends beyond base 702, and then into tendon 736 to secure or assist in securing device 700 to the tendon. In this embodiment, the middle and edge portions are configured to help distract a humeral head in abduction.

In other embodiments (not shown), a device may be provided with lumens having a steeper or shallower angle relative to tendon 736. While the exemplary device 700 shown in FIGS. 12-14 employs six anchors, other devices constructed in accordance with aspects of the present description may be provided with a smaller or larger number of anchors. In other embodiments, sutures, staples, adhesive and/or other fasteners may be used in conjunction with or instead of anchors 730 to secure device 700 to the underlying tissue. Preformed holes may also be provided in sheet 724 to allow anchors 730 to pass through. In other embodiments, sheet 724 may be omitted. In still other embodiments, the device may have more or less of a cup shape, be generally flat, or inverted such that the anchors emerge from the convex side rather than the concave side. The device may be oblong, curved in only one dimension, or be saddle-shaped, depending on the particular anatomy it is designed to protect.

An implantable device such as previously described may be placed over a partial tear in a tendon. In some embodiments, the device may be implanted over a tendon having micro-tear(s), abrasions and/or inflammation. Left untreated, minor or partial tendon tears may progress into larger or full tears. According to aspects of the present invention, a small or partial tear may be treated by protecting it with an implantable device as described above. Such early treatment can promote healing and prevent more extensive damage from occurring to the tendon, thereby averting the need for a more involved surgical procedure.

The implanted device may serve to protect a tendon from a stimulus. The stimulus may comprise one or more of the following: pressure, friction, temperature, electrical or chemical stimulus. In some embodiments, the device does not supplant or share any substantial load borne by a tendon, but serves to protect the tendon to facilitate healing.

In some embodiments, a bursa overlying a tendon is left substantially intact as the device is implanted over the tendon. This may be accomplished by creating a small incision or puncture through one wall of the bursa through which the device delivery cannula may be placed. The bursa may be filled with saline or similar fluid during the procedure to keep it inflated, thereby providing sufficient operating space for deploying and attaching the implantable device. After the device is implanted and the delivery cannula is removed, the opening in the bursa may be closed, such as with one or more sutures. Alternatively, it is believed that the bursa may form closure tissue by itself post-operatively. Such bursa growth may be stimulated by movement of the tendon and/or bursa relative to surrounding tissue.

In other embodiments, a portion or all of the bursa may be removed during the implantation procedure. In these embodiments, the implantable device may be sized and positioned to facilitate the bursa reforming naturally in its original location after the procedure.

As previously indicated, the implantable device may comprise an absorbable material. In some embodiments, the purpose of the device is to protect an injured portion of a tendon during healing, provide a scaffolding for new tissue growth, and/or temporarily share some of the tendon loads. The device may induce additional tendon tissue formation, thereby adding strength and reducing pain, micro strains and inflammation. When the device is applied to a structurally intact, partially torn tendon, the initial loading of the device may be carried by native tendon tissue until collagen is formed during the healing process. In some embodiments, organized collagen fibers are created that remodel to neo tendon with cell vitality and vascularity. Initial stiffness of the device may be less than that of the native tendon so as to not overload the fixation while tendon tissue is being generated.

The implantable device may be configured to allow loading and retention of biologic growth factors. The device and/or the growth factors may be configured to controllably release the growth factors. The device may be configured to allow transmission of body fluid to remove any degradation bi-products in conjunction with a potential elution profile of biologics. The device should degrade over time with minimal inflammatory response. For example, particulate matter that may result from degradation should not generate synovitus in the joint.

In one exemplary embodiment, the implantable device has a diameter of about 22 mm, and has directionally specific mechanical properties. In another embodiment, the device is generally rectangular with a width of about 20 mm, a length of about 40 mm, and a thickness of about 1 mm. In another embodiment, the device has a length of about 30 mm. These latter two arrangements provide a 20 mm2 cross-sectional area transverse to the load direction.

It is desirable in some situations to generate as much tissue as possible within anatomical constraints. In some cases where a tendon is degenerated or partially torn, tendon loads are relatively low during early weeks of rehabilitation. For example, the load may be about 100 N. The strain in the tendon due to the load during rehabilitation can be about 2%. In some of these cases, the implantable device can be designed to have an ultimate tensile strength of at least about 5 MPa. The tensile modulus can be designed to be no more than about 50 MPa and no less than about 20 MPa. The compressive modulus can be designed to be at least about 0.5 MPa. With a tensile modulus of 50 MPa, in order for the scaffold to strain 2% in conjunction with the degenerated tendon, the stress on the scaffold will be about 1.0 MPa. With an ultimate tensile strength of 5 MPa, the strength of the scaffolding of the implantable device when first implanted will be about five times the expected loads. With a cross-sectional area of 20 mm2, the load on the scaffold will be 20 N. Thus, from a load sharing perspective, the scaffold will carry about 20% of the load to experience 2% strain.

A published value for the compressive modulus of the supraspinatus tendon is in the range of 0.02-0.09 MPa (J Biomech Eng 2001, 123:47-51). The scaffold provided by the implantable device should have a higher compressive modulus than the tendon to prevent collapse of pores in the scaffold. A compressive modulus of 0.5 MPa would be about five times greater than the tendon.

The tissue within the device scaffold will typically be developing and organizing during the first one to three months after implantation, so load sharing with the scaffold is desired in some embodiments. After three months the tissue will typically be remodeling, so the mechanical properties of the scaffold should gradually decline to zero to enable the new tissue to be subjected to load without the scaffold bearing any of the load. If the scaffold loses modulus faster than it loses strength, then the relative loads on the scaffold will be less at three months than when first implanted. For example, if the modulus of the scaffold drops 50% to 25 MPa at three months, then 2% strain of the scaffold would require a stress of only about 0.5 MPa. At the same time, if the strength of the scaffold drops about 30% to 3.5 MPa, then the strength of the scaffold will be about seven times the anticipated loads at three months, compared to about five times when first implanted. Therefore, with the design criteria provided above, tensile failure of the scaffold during the first three months should be unlikely. Accordingly, the following specifications for degradation rate are recommended in some embodiments: an ultimate tensile strength of at least 70% strength retention at three months; tensile and compressive modulus of at least 50% strength retention at three months; and no minimum specification for strength and modulus at 6 months. The device may be designed to have a degradation profile such that it is at least 85% degraded in less than 1 to 2 years after implantation.

Cyclic creep is another design constraint to be considered in some embodiments. A strain of about 2% with a 40 mm long scaffold will result in an elongation of about only 0.8 mm. Therefore, very little cyclic creep can be tolerated in these embodiments to ensure that the scaffold will undergo strain with each load cycle. A test where a proposed scaffold design is cyclically strained to 2% at 0.5 Hz for 1 day provides 43,200 cycles, which likely exceeds the number of cycles experienced in three months of rehabilitation of a patient's joint. Incorporation of relaxation times should be considered in such testing. In some embodiments, a maximum of about 0.5% creep is an acceptable specification.

Material(s) used in the implanted device should be able to withstand the compression and shear loads consistent with accepted post surgical shoulder motions. The perimeter of the device may have different mechanical properties than the interior of the device, such as for facilitating better retention of sutures, staples or other fastening mechanisms. The material(s) may be chosen to be compatible with visual, radiographic, magnetic, ultrasonic, or other common imaging techniques. The material(s) may be capable of absorbing and retaining growth factors with the possibility of hydrophilic coatings to promote retention of additives.

While the systems, kits and methods disclosed above have been discussed relative to protecting tendons in shoulder joints, they may also be utilized to protect tendons in other articulating joints such as the knee, elbow and ankle.

While exemplary embodiments of the present invention have been shown and described, modifications may be made, and it is therefore intended in the appended claims to cover all such changes and modifications which fall within the true spirit and scope of the invention.

What is claimed is:

1. A method of implanting an implant in a shoulder region of a patient comprising:
   inserting a distal end of an implant delivery device into a shoulder region of the patient proximate a supraspinatus muscle, the implant delivery device comprising:
   a sheath defining a lumen; and
   an implant disposed within the lumen of the sheath;
   transitioning the implant from an undeployed state within the sheath to a deployed state outside of the sheath;
   positioning the implant over a partial thickness tear of a supraspinatus tendon of the patient;
   attaching the implant to the supraspinatus tendon of the patient while the implant is positioned over the partial thickness tear of the supraspinatus tendon of the patient.

2. The method of claim 1, further comprising inserting the distal end of the implant delivery device into a subacromial bursa of the patient.

3. The method of claim 1, further comprising attaching the implant to the supraspinatus tendon using staples.

4. The method of claim 1, further comprising attaching the implant to the supraspinatus tendon using an adhesive.

5. The method of claim 4, wherein the implant comprises a least one channel and a plurality apertures, and the method further comprising:
   injecting the adhesive into the at least one channel.

6. The method of claim 5, wherein the adhesive elutes through the plurality of apertures after being injected into the at least one channel.

7. The method of claim 1, further comprising attaching the implant to the supraspinatus tendon such that at least a portion of the implant overlays the supraspinatus tendon and at least a portion of the implant overlays a humerus bone.

8. The method of claim 1, wherein the implant comprises a bioabsorbable material.

9. The method of claim 1, further comprising retracting the sheath to transition the implant from the undeployed state to the deployed state.

10. The method of claim 1, wherein the implant comprises:
   a first layer having a sliding surface; and
   a second layer opposite the first layer and configured to engage the supraspinatus tendon, the second layer comprising a biocompatible material and a plurality of pores for encouraging tissue growth.

11. A method of attaching an implant to a supraspinatus tendon of a patient comprising:
   inserting a sheet-like implant into a subacromial bursa of the patient;
   positioning the implant so that at least a portion of the implant covers a partial thickness tear of the supraspinatus tendon; and
   securing the implant to the supraspinatus tendon while at least a portion of the implant is covering the partial thickness tear of the supraspinatus tendon.

12. The method of claim 11, further comprising positioning the implant so that at least a portion of the implant covers a humerus bone.

13. The method of claim 11, further comprising:
   inserting the implant into the subacromial bursa in a folded configuration; and
   unfolding the implant while in the subacromial bursa.

14. The method of claim 13, wherein the implant is inserted into the subacromial bursa within a sheath of a delivery device.

15. The method of claim 11, wherein the implant comprises at least one channel in fluid communication with a plurality of apertures on a tendon-engaging surface of the implant.

16. The method of claim 11, wherein securing the implant to the supraspinatus tendon comprises inserting one or more staples through the implant and into the supraspinatus tendon.

17. A method of treating a rotator cuff of a shoulder of a patient comprising:
   inserting a distal end of an implant delivery device into a subacromial bursa within the shoulder of the patient, the implant delivery device comprising:
      a sheath; and
      an implant disposed within the sheath in a folded configuration;
   advancing the implant beyond the distal end of the implant delivery device into the subacromial bursa;
   transitioning the implant from the folded configuration to an unfolded configuration within the subacromial bursa;
   positioning the implant so that at least a portion of the implant covers a partial thickness tear of a supraspinatus tendon of the patient; and
   attaching the implant to the supraspinatus tendon while at least a portion of the implant is covering the partial thickness tear of the supraspinatus tendon of the patient.

18. The method of claim 17, where the implant is attached to the supraspinatus tendon by inserting one or more staples through the implant and into the supraspinatus tendon.

19. The method of claim 17, further comprising positioning the implant so that at least a portion of the implant covers a humerus bone of the patient.

20. The method of claim 17, where in the unfolded configuration the implant assumes a concave shape.

* * * * *